United States Patent [19]

Brady et al.

[11] Patent Number: 6,124,124
[45] Date of Patent: Sep. 26, 2000

[54] OXIDATION IN SOLID STATE OF OXIDIZABLE GALACTOSE TYPE OF ALCHOHOL CONFIGURATION CONTAINING POLYMER

[75] Inventors: Richard Lee Brady, Wilmington; Raymond Thomas Leibfried, Sr., Newark; Tuyen Thanh Nguyen, Wilmington, all of Del.

[73] Assignee: Hercules Incorporated, Wilmington, Del.

[21] Appl. No.: 09/001,789

[22] Filed: Dec. 31, 1997

[51] Int. Cl.⁷ ..................................... C12N 9/04
[52] U.S. Cl. ................. 435/190; 435/178; 435/192; 435/274
[58] Field of Search ................... 435/178, 190, 435/192, 274

[56] References Cited

U.S. PATENT DOCUMENTS

| | | | |
|---|---|---|---|
| 3,236,832 | 2/1966 | Opie et al. | 260/209 |
| 3,297,604 | 1/1967 | Germino | 260/17.4 |
| 3,691,153 | 9/1972 | Vemuri | 260/209 R |
| 5,262,151 | 11/1993 | Montgomery | 424/50 |
| 5,270,033 | 12/1993 | Montgomery | 424/50 |
| 5,554,745 | 9/1996 | Chui et al. | 536/52 |

*Primary Examiner*—Francisco Prats
*Attorney, Agent, or Firm*—Robert O'Flynn O'Brien

[57] ABSTRACT

Composition comprising oxidizable galactose type of alcohol configuration containing polymer (such as guar) which is in solid state and galactose oxidase. Application of such oxidized polymers in the papermaking process results in superior paper strength characteristics.

28 Claims, No Drawings

OXIDATION IN SOLID STATE OF OXIDIZABLE GALACTOSE TYPE OF ALCHOHOL CONFIGURATION CONTAINING POLYMER

BACKGROUND OF THE INVENTION

1. Field of the Invention

The present invention relates to oxidation of oxidizable galactose type of alcohol configuration containing polymer which is in solid state and more particularly it relates to the oxidation of guar gum solids with galactose oxidase yielding superior paper strength additives.

2. Description of the Prior Art

The product of the oxidation of aqueous solutions of guar gum and other galactose bearing polysaccharides using galactose oxidase enzyme was disclosed by F. J. Germino in U.S. Pat. No. 3,297,604. The aldehyde bearing oxidized products are separated by precipitation from the aqueous solutions used for the enzyme reactions. Germino disclosed the use of the oxidized products in the manufacture of paper. The aldehyde bearing oxidized products were disclosed to be also suitable for use to crosslink polyamino polymers, polyhydroxy polymers, and proteins.

C. W. Chiu, et.al., U.S. Pat. No. 5,554,745, discloses (1) the preparation of cationic galactose containing polysaccharides and (2) the enzymatic oxidation in aqueous solution of the cationic galactose containing polysaccharides with galactose oxidase. The oxidized cationic polysaccharides are disclosed to improve the strength characteristics of paper.

SUMMARY OF THE INVENTION

According to the present invention there is provided a composition comprising oxidizable galactose type of alcohol configuration containing polymer which is in solid state and galactose oxidase. Oxidizable galactose type of alcohol configuration containing polymer can be galactomannan gums or their ether derivatives, arabinogalactan gums or their ether derivatives, other gums or their ether derivatives, galactoglucomannan hemicelluloses or their ether derivatives and synthetically or enzymatically modified polymers. Preferably means that can decompose hydrogen peroxide such as catalase, and oxidation promoting chemical can be present also.

The present invention also provides partially oxidized oxidizable galactose type of alcohol configuration containing polymer in free flowing particulate form and galactose oxidase in substantially active form and movable gels of oxidized galactose type of alcohol configuration containing polymer and galactose oxidase.

There is also provided the process of making paper with oxidizable galactose type of alcohol configuration containing polymer and galactose oxidase composition and the paper so made.

Further according to the present invention there is provided a process comprising providing oxidizable galactose type of alcohol configuration containing polymer which is in solid state and galactose oxidase and contacting them.

DETAILED DESCRIPTION OF THE INVENTION

It has surprisingly been discovered that polymer containing groups having an oxidizable galactose type of alcohol configuration such as guar, can be oxidized in the solid state with galactose oxidase. The phrase "solid state" as used in the present application means that the polymer is in particulate form, i.e., is composed of discrete particles, which are preferably visible to the naked eye. This definition includes polymer particles that are swollen, i.e., solvated by galactose oxidase solution or catalase solution. When the oxidizable galactose type of alcohol group containing polymer, galactose oxidase and catalase of the present invention is applied in the papermaking process, it results in superior paper strength characteristics.

The groups having an oxidizable galactose alcohol type of configuration can be described by the following chemical structures:

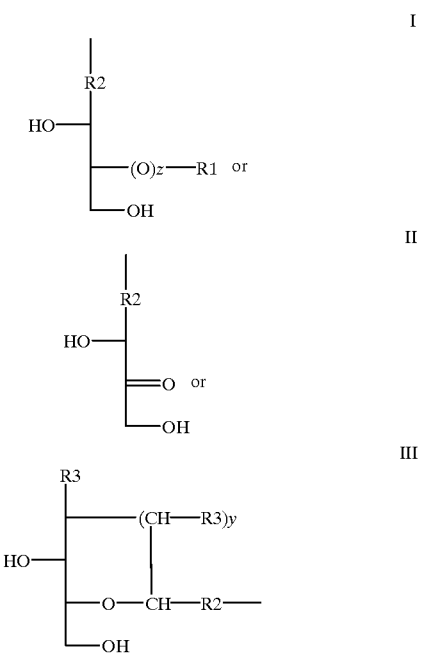

where;

R1=an alkyl group of the formula $C(n)H(2n+1)$ where n=0–20;

z=0,1;

R2=a linking group composed of an alkylene, or an aromatic alkylene, or an alkylene ether, or an alkylene ester, or an alkylene amide, or an alkylene urethane diradical. Such linking groups have a total number of carbon from 2 to 20;

R3=—H, —OH, —OCH3, —OC2H5,—OC3H7,—OC4H9, —OOCR5 (where R5=alkyl radical of 1 to 5 carbons), —NH2, —NH—CO—R5;

and y=0,1.

The oxidizable galactose type of alcohol configuration containing polymers can be galactomannan gums or their ether derivatives, arabinogalactan gums or their ether derivatives, other gums or their ether derivatives, galactoglucomannan hemicelluloses or their ether derivatives and synthetically or enzymatically modified polymers. Preferred galactomannan gums are guar, locust bean, tara and fenugreek. Preferred arabinogalactan gums are arabic, larch and tragacanth gums. Preferred synthetically or enzymatically modified polymers are galactose deficient polysaccharides, polyacrylamides, polyacrylates, polyamides, polyvinyl alcohol, and polyvinyl acetate. Most preferred such polymers are starch and polyacrylates. The phrase "galactose deficient" as used in the present application means that the oxidizable galactose type of alcohol configuration containing polymer it refers to contains less than 20% of oxidizable galactose type alcohol configuration based on the weight of the oxidizable galactose type of alcohol configuration containing polymer. Preferred other gums are carubin, lichenan, tamarind and potato galactan. Most preferred oxidizable galactose type of alcohol configuration containing polymers are guar gum and its ether derivatives such as cationic, anionic, amphoteric, hydroxypropyl, dihydroxypropyl and hydroxyethyl guar.

Synthetically or enzymatically modified polymers can be obtained by attaching the oxidizable galactose type of alcohol configuration to polymers or by polymerizing a monomer that contains oxidizable galactose type of alcohol configuration.

The oxidized galactose type of alcohol configuration containing polymer component of the present invention has at least about 5 mole % of its oxidizable galactose type of alcohol configuration oxidized to aldehyde. Preferably, at least about 25 mole % and most preferably at least about 50 mole % of such alcohol has been oxidized to aldehyde. The oxidizable galactose type of alcohol configuration containing polymer used for oxidation can range over a wide molecular weight range. It can be high molecular weight, or alternatively it can be a depolymerized (reduced viscosity) polymer. Generally, the lower limit of the weight average molecular weight of the oxidizable gallactose type of alcohol configuration containing polymer can be about 5,000. The upper limit of the weight average molecular weight of the oxidizable galactose type of alcohol configuration containing polymer can be about 5,000,000. Preferably, the molecular weight range as indicated by room temperature Brookfield viscosity is at least about 15 cps at 2 weight percent solution in water, most preferably, at least about 100 cps at 1 weight percent solution in water. Preferably, the room temperature Brookfield viscosity can be up to about 10,000 cps most preferably up to about 6,000 cps at 1 weight percent solution in water,. (Measured in Brookfield LVT viscometer with small sample adapter, 25° C., spindle 31, speed 3 rpm).

Guar is preferred as the oxidizable galactose type of alcohol configuration containing polymer for use in the present invention. The present application refers to guar specifically in certain instances, however, the person of ordinary skill in art will recognize that these teachings apply to the oxidizable galactose type of alcohol configuration containing polymer in general.

Glactose oxidase (EC 1.1.3.9) is a copper oxidase which converts the oxidizable galactose type of alcohol configuration to the corresponding aldehyde group (thus producing oxidized galactose) by reducing oxygen to hydrogen peroxide. The copper must be in the correct oxidation state ($Cu^{2+}$) to perform this oxidation and the copper ion must be retained in the galactose oxidase.

Dissolved copper ions can be used beneficially in the processing and use of galactose oxidase according to Mazur (Enzymes in Carbohydrate Synthesis, Feb. 7, 1991, pg 100) to prevent the loss of copper from the protein.

If the galactose oxidase solution is stored anaerobically with any oxidizable substrate, it can become inactive. Galactose oxidase can be reactivated by oxidizing the copper with reagents such as potassium fenicyanide or the copper can be kept in the proper oxidation state by adding peroxidase and aerating the enzyme solution. If the enzyme solution is stored anaerobically with any oxidizing substrate, it becomes inactive and must be reactivated with peroxidase and oxygen. Another way to oxidize the copper in galactose oxidase would be by electrochemical oxidation.

Galactose oxidase can be obtained by any suitable manner, e.g., by fermenting various wild type and cloned fungi but is usually obtained from Fusarium spp (NRRL 2903). Cultures may also be obtained from the American Type Culture Collection under Dactylium dendroides ATCC 46032 and they are successfully fermented under the procedure of Tressel and Kosman. Methods in Enxymology, Vol 89 (1982), pg 163–172. The gene for active forms of the enzyme have been expressed in *E.coli* and Aspergillus and this development may lead to more stable and active forms of the enzyme as well as much greater production levels. The gene or improved forms will also be expressed in plants which can be harvested to give higher levels of enzyme without the threat of enzyme destruction by proteases in a fermentation broth.

The enzyme can also be expressed by other organisms including: *Gibberella fujikoroi, Fusarium graminearum*, and *Bettraniella porticensis*.

An International Unit (IU) of galactose oxidase will convert one microequivalent of the oxidizable galactose type of alcohol configuration containing polymer to aldehyde per minute at 25° C. and pH 7.0. The unit can be measured by coupled assays where the by-product $H_2O_2$ is used by peroxidases to oxidize dye precursors, giving a chromophore. The production of the chromophore is measured by light absorbance at a wavelength suitable to the dye used (o-tolidine, 425 nm; o-dianisidine, 436 nm; 2,2'-azinobis(3-ethylbenzo-thiazoline-6-sulfonic acid), diammonium salt (ABTS), 405 nm). The method using the ABTS dye is used to determine International Units (IU).

The galactose oxidase should be sufficiently stable, i.e. active, in the composition made up of oxidizable galactose type of alcohol configuration containing polymer, galactose oxidase and optionally catalase to catalyze the oxidation of the oxidizable galactose type of alcohol configuration to aldehyde during mixing, storage and upon dissolution in water. This catalytic oxidation with galactose oxidase is enhanced if an oxidant for the galactose oxidase is present in the composition. The oxidant promotes the formation of the active oxidized form of galactose oxidase at its catalytic site. The oxidant can be a soluble salt such as potassium ferricyanide or it can be a peroxidase such as soybean peroxidase or horseradish peroxidase.

Preferably the oxidation of oxidizable galactose type of alcohol configuration containing polymer with galactose oxidase is carried out in the presence of means to decompose the hydrogen peroxide generated during the conversion of the oxidizable galactose type of alcohol configuration to aldehyde. Preferably the means to decompose hydrogen peroxide is catalase.

Other metal complexes and compounds can also be used to decompose the hydrogen peroxide formed in the oxidation reaction. Chemicals that will accomplish redox chemistry with hydrogen peroxide are iron complexes, e.g., with polyamines (notably triethylenetetramine) and persulfates.

Increased levels of oxidation and corresponding increase in paper strength characteristics is the subject of companion application filed . . . (Hercules Docket No. DEV 5522 "Use of Oxidation Promoting Chemicals in Oxidation of Oxidizable Galactose Type of Alcohol Configuration Containing Polymers" by R. L. Brady and R. T. Leibfried), the disclosure of which is hereby incorporated by reference.

Preferably the oxidation promoting chemical is organic carboxylate compound, organic heterocyclic compound, chlorinated organic compound and/or quaternary amine compound. Most preferably the organic carboxylate compound is sorbic acid, benzoic acid, toluic acid, phthalic acid and their corresponding salts, the organic heterocyclic compound is 1,2-benzisothiazolin-3-one, and/or 2-methyl-4- isothiazoline-3-one, the chlorinated organic compound is 5-chloro-2-methyl-4-isothiazolin-3-one, and quaternary amine compound is cetyltrimethylammonium bromide and/ or epoxy quaternary amines.

When the galactose oxidase is also applied in solid state the lower limit of the oxidizable galactose type of alcohol configuration can be about 50% based upon the weight of the composition. Preferably the lower limit is about 70% and most preferably it is about 85% when the galactose oxidase is in solid state. When the galactose oxidase is also applied in solid state the upper limit of the oxidizable galactose type of alcohol configuration containing polymer can be about 100% based upon the weight of the composition. Preferably it can be about 98% and most preferably about 95%.

When the solid oxidizable galactose type of alcohol configuration containing polymer is contacted with galactose oxidase in aqueous medium the lower limit of the oxidizable galactose type of alcohol configuration containing polymer can be about 4%, preferably about 6% and most preferably about 8%. In this instance the upper limit of the oxidizable galactose type of alcohol configuration containing polymer can be about 500/o, preferably about 30% and most preferably about 20%, all based upon the weight of the composition.

The lower limit of the galactose oxidase can be about 10 units per gram of oxidizable galactose type of alcohol configuration containing polymer. Preferably the lower limit is about 25 and most preferably about 35 units per gram of oxidizable galactose type of alcohol configuration containing polymer. The upper limit of the galactose oxidase can be about 3,000 units per gram of oxidizable galactose type of alcohol configuration containing polymer, preferably about 2,000 and most preferably about 1,000 units per gram of oxidizable galactose type of alcohol configuration containing polymer.

The lower limit of catalase can be about 1, preferably about 50 and most preferably about 100 units of catalase/ unit of galactose oxidase. The upper limit of catalase can be about 10,000, preferably about 5,000 and most preferably about 1,000 units of calatase/unit of galactose oxidase. One (1) unit of catalase will convert a micromole ($10^{-6}$ mole) of hydrogen peroxide to water and oxygen per minute at pH 7.0 and 25° C.

The lower limit of the oxidation promoting chemical can be about 0.1% based on the weight of oxidizable galactose type of alcohol configuration containing polymer. Preferably the lower limit of the oxidation promoting chemical is 0.5% and most preferably it is 1%. The upper limit of the oxidation promoting chemical can be about 5% based on the weight of oxidizable galactose type of alcohol configuration containing polymer, preferably about 3% and most preferably about 2%.

The product of the present invention can be a free flowing particulate composition of partially oxidized galactose type of alcohol configuration containing polymer and galactose oxidase in substantially active form and up to about 30%, based upon the weight of the composition, of water. Generally the free flowing particulate composition will contain at least about 5% water. Alternatively, the product of the present invention can be a movable gel composition containing oxidized galactose type of alcohol configuration containing polymer, galactose oxidase in substantially active form and up to about 90%, preferably up to about 50%, based upon the weight of the composition, of water. The phrase "movable gel" as used in the present application means swollen gel particles that can be stirred or pumped. The phrase "substantially active form" as used in the present application means that at least about 10% by weight of the galactose oxidase is in active form. Preferably at least about 30%, and most preferably at least about 50% by weight of the galactose oxidase is in active form.

The oxidation of oxidizable galactose type of alcohol configuration containing polymers using galactose oxidases can be performed efficiently in the solid state. The oxidation can be carried out [1] by air dispersion of oxidizable galactose type of alcohol configuration containing polymer particles and galactose oxidase using blenders, (e.g., Oster, Waring, Turbulator) [2] by dry and wet grinding of oxidizable galactose type of alcohol configuration containing polymer and galactose oxidase solids and [3] in suspension of solid oxidizable galactose type of alcohol configuration containing polymer in aqueous solution of galactose oxidase with or without the presence of nonsolvents for the oxidizable galactose type of alcohol configuration containing polymer. This latter method is the preferred mode for the oxidation process of the present invention. The phrase "nonsolvent" for the oxidizable galactose type of alcohol configuration containing polymer in the context of the present application means that less then 0.1% by weight of the oxidizable galactose type of alcohol configuration containing polymer dissolves in the nonsolvent at room temperature. Nonsolvents suitable for use in the present invention can be water soluble, organic compounds having a molecular weight up to about 500, such as alcohols, ketones and ethers. Preferably the nonsolvents are alcohols and ketones. Most preferably the nonsolvent is methanol.

Galactose oxidase and catalase solids can be air dispersed unto guar powder in 15 seconds in an Oster blender to give a composition that is stable at room temperature for months. This dispersion process can be carried out with up to about 50% water being present on the guar. The galactose oxidase and catalase may be added in solid form or in solution. Partial oxidation occurs in the oxidizable galactose type of alcohol configuration containing polymer solids with time in storage, i.e., at least about 10 mole % of the oxidizable galactose type of alcohol configuration of the oxidizable galactose type of alcohol configuration containing polymer (e.g., guar gum) is oxidized to aldehyde. Large continuous blenders can produce this composition at 2000 lbs/hr of solids in a small operating area in a very efficient manufacturing mode.

The preferred method for making the more highly oxidized oxidizable galactose type of alcohol configuration containing polymer particle suspensions of the present invention is to suspend solid oxidizable galactose type of alcohol configuration containing polymer particles of different size (i.e., from microns to seed splits) in water containing galactose oxidase, catalase and dissolved oxygen. The solid particles swell with water that contains galactose oxidase, catalase, and dissolved oxygen providing good conditions for oxidation. The oxidation rate can be enhanced by sparging pure oxygen into the reactor and further enhanced by sparging oxygen under several atmospheres of pressure. If relatively dry polymer particles are contacted with fully oxygenated water under pressure as well as oxidase and catalase, the swollen solids can contain the oxygen needed for reaction and the need for further oxygen diffusion is decreased greatly. This operation may be carried out in a reinforced in-line mixer with a screw feed for the solids and oxygen eduction for the aqueous feed.

The mixing intensity in the suspension must be carefully controlled to avoid excessive dissolution (i.e., less than 0.1% based upon the weight of the aqueous suspension of oxidizable galactose type of alcohol configuration containing polymer is dissolved) and any formation of a continuous gel. The somewhat gelatinous swollen solid particles may be tumbled, stirred nonintensively or pumped (diaphragm, peristaltic) to improve oxygen mass transfer and product transfer without a significant increase in the viscosity of the suspension. An in-line mixer with pumping in a loop at a low Reynolds number would be an efficient low cost mode for carrying out the oxidation of this invention. The tumbling mode can be carried out in a Rotocone reactor which will preserve the integrity of the swollen particles throughout.

The most preferred mode is a suspension of oxidizable galactose type of alcohol configuration containing polymer in aqueous solution of galactose oxidase and catalase containing a nonsolvent for the oxidizable galactose type of alcohol configuration containing polymer.

Optionally the suspension of oxidized oxidizable galactose type of alcohol configuration containing polymer can be dried and ground.

The oxidizable galactose type of alcohol configuration containing polymer can be contacted with galactose oxidase by dry mixing the ingredients which preferably also contain catalase or its functional equivalent and an oxidation promoting chemical. The phrase "dry mixing" as used in the present application means contacting oxidizable galactose type of alcohol configuration containing polymer particles having up to about 50 weight % of water with solid galactose oxidase or with an aqueous solution of galactose oxidase such that the resulting mixture contains up to about 50 weight % of water. Alternatively, the solid polymer containing galactose can be contacted with galactose oxidase in an aqueous medium in which less than about 0.1% by weight of the polymer containing galactose is dissolved. As another variation the polymer containing galactose can be contacted with galactose oxidase in aqueous medium also containing a nonsolvent for the oxidizable galactose type of alcohol configuration containing polymer provided that less than about 0.1% by weight of polymer containing galactose is dissolved in such aqueous medium. After the desired extent of oxidation has taken place, the solids can be filtered out and the liquids can be reused.

An alternative process for carrying out the oxidation reaction involves swelling the guar seed splits in aqueous suspension. The splits may be borated on the surface by reaction with sodium borate at a pH of about 9 or higher to prevent premature dissolution. The dried borated splits are suspended in an activated solution of galactose oxidase and catalase and sufficient oxygen is provided to carry the oxidation to the level desired. The splits can be swollen with an enzyme solution that is saturated by pure oxygen under pressure to provide sufficient oxygen to carry the oxidation to the desired extent inside the splits. Another way to provide supplemental oxygen is to add a dilute solution of hydrogen peroxide to the splits which have been previously swollen with the galactose oxidase and catalase solution. The catalase in the swollen splits decomposes the hydrogen peroxide to provide oxygen for the reaction.

The enzyme solutions may be applied to the guar that is in powder form, and the rate of the enzyme reaction is related to the size of the powder particles. The enzyme solution may be used to swell dry powders and splits, possibly putting enzymes into the particles as well as on the surface. The enzymatic oxidation proceeds during storage of these powders and guar splits where 10–90% of the composition is actually water. The presence of water miscible solvents that do not dissolve guar (i.e., nonsolvents for guar) can be used to prevent excessive dissolution (i.e. more than about 0.1 weight %) of guar particles which would give solids handling problems.

The advantages of air dispersion solid state oxidation are: (1) rapid processing by air blending, (2) minimal or even no drying energy needed to create flowable powder products, (3) no need to ship excess weight in the form of water and (4) the user can handle the product as a free flowing particulate composition, e.g. powder and prepare solutions to his specifications.

The aqueous suspension process will permit higher levels of oxidation in an easily stirred reaction mass where oxygen transfer is sufficient to carry out higher levels of oxidation. After the reaction water can be removed rather easily by centrifuging or filtering the solids followed by drying in hot air and grinding. The advantages are (1) use of minimal water, (2) higher oxidation levels and (3) ease of powder production in existing plant equipment. The aqueous slurry can produce a swollen hydrogel form that can be shipped in that form for rapid preparation of solutions. The user would save time since the oxidized polymer particles are already hydrated and the solution would form in minutes requiring less volume in the solution make-up facility.

The oxidation of guar and other oxidizable galactose type of alcohol configuration containing polymers in solution as done in the prior art references gives very high viscosity solutions at low polymer concentrations. The concentration of guar must be kept under 1% to prevent an intractable gel from forming during the oxidation. Also, if a dry product is desired, a large amount of water soluble nonsolvent (50% or more based on water) for the oxidizable galactose type of alcohol configuration containing polymer must be added to precipitate the oxidized product prior to filteration and drying. A large distillation equipment is required to recover the nonsolvent. The manufacturing facility must handle very large volumes of water and nonsolvents to recover a small amount of product (300/1 liquid/solid). Some provision must be made to keep the oxidized solution from gelling by the formation of intermolecular hemiacetals and reagents to stabilize the solution must be added in significant amounts (alcohols, sodium bisulfite, amines, etc.). This requires the recovery and recycling of more reactants.

The oxidized product, e.g. oxidized guar, gives an increase in paper dry tensile strength over the corresponding unoxidized material. In addition to dry strength, properties such as z-direction tensile strength, Scott bond strength, Mullen burst, ring crush, tensile energy absorption (TEA), fracture toughness, wet strength, and temporary wet strength can also be improved by using the oxidized product.

For the Examples the performance of the oxidized oxidizable galactose type of alcohol configuration containing polymer, e.g. oxidized guar, in paper was determined by (1) a lap shear test on cellophane, and (2) laboratory handsheet preparation and tensile testing. The lap shear test was performed as follows:

1. 100–200 g of 0.01% or 0.001% solution of the additive was prepared in an aluminum pan with deionized water.
2. Sheets of cellophane film (product 195 PUT 002, available from Flexel, Inc.) 1 mil×4 in×3 in were cut with scissors. The long direction was the film machine direction and ultimately became the tensile direction in the lap shear test.
3. 4 sheets of film were soaked in the solution for 1 min. The sheets were removed and placed on a 100 mesh papermaking screen so that 2 pairs of overlapped films were created. Overlaps were controlled as well as possible to 2.5 mm. A paper towel was under the screen to absorb excess solution.
4. The films were touched briefly on the surface with a paper towel to remove surface moisture. A second screen was then placed on top to sandwich the film between screens. ⅛ in thick aluminum frames were placed on top and bottom of the screens to hold the screens closer together but allow air flow to the film.

5. The film/screen/frame configuration was placed in a 105° C. oven and the films dried for 30 min. The films were then removed and allowed to cool to room temperature. Strips were cut with scissors in the long direction of the overlapped films, with the overlap in the center. Typical strip widths were 8–12 mm and lengths around 5 inches.

6. Lap shear testing was done initially on an Instron 1000 using a gauge length of 1.5 in and speed 2 in/min. Masking tape tabs were used on the samples to prevent breakage of the film in the grips. The width and overlap length for each sample were recorded before testing. Overlap areas were inspected visually for debonding before the test. Any samples that were debonded due to drying stresses were not tested. Any samples that failed outside the overlap area were considered invalid.

7. The maximum load (load at break) was read from the Instron and divided by the overlap area to give the bond strength. Average bond strength and average overlap were then used to normalize to 2.5mm overlap. Five samples or more were generally used for the averages.

8. Later on, an Alwetron TH1 Tensile Tester (available from Lorentzen and Wettre USA, Inc.) was used to test the samples. In this case, no tabs were used because of different style grips. Gauge length was 100 mm and speed was 90 mm/min. It was confirmed that the two machines gave equivalent numbers.

Handsheets were made on a Noble and Wood Sheet Machine (Noble and Wood Machine Co., Hoosick Falls, N.Y.) using standard hard water at a controlled pH of 7.5. Standard hard water (50 ppm alkalinity and 100 ppm hardness) was made by mixing deionized water with $CaCl_2$ and $NaHCO_3$. Control of pH was achieved by using NaOH or $H_2SO_4$. Bleached kraft pulp was beaten to a Canadian Standard Freeness of 455 at a consistency of 2.5 weight %. The beaten pulp was added to the proportioner at a controlled level (depending on final desired basis weight) and diluted to 18 liters with standard hard water. For 80 lb/3000 $ft^2$ basis weight, 4000 ml of pulp mixture was used. Chemical additions and pH adjustments were made to the proportioner as desired, and with continuous mixing.

A clean and wetted 100 mesh screen was placed on the open deckle box, which was then closed. Standard hard water and 920 ml of pulp mixture from the proportioner were then added to the deckle box, and dashed. The water was then drained from the box, and the sheet removed. The sheet was wet pressed between felts with press weights adjusted to give a solids content of 33–34%. The sheet and screen were then placed on a drum dryer, which was adjusted to a temperature of 228–232° F. and throughput time of 50–100 sec, depending on basis weight. Final sheet moisture contents were 3–5%. Five sheets minimum were tested for each experimental set.

Tensile testing was done on the handsheets according to TAPPI Method T 494 om-88 ("TAPPI Test Methods", TAPPI Press, Atlanta, Ga., 1996).

The scope of this invention as claimed is not intended to be limited by the following examples, which are given merely by way of illustration. All parts are by weight unless otherwise indicated.

EXAMPLE 1

This example illustrates the treatment of cationic guar splits with catalase and galactose oxidase enzymes to prepare an oxidized guar product.

Intact cationic guar splits were used at an initial 35.6% solids level (64.4% water) in this Example. The apparatus used was a two ounce wide-mouth jar on a small roller mill, and a 2 inch polytetrafluoroethylene-coated magnetic stir bar was added to provide extra mixing as the jar rolled. The splits (5.63 g=2 g dry) were mixed with catalase (0.374 g Sigma C40, available from Sigma Chemical Company, 7854 IU) using a spatula and rolled in the jar overnight. Next, galactose oxidase (0.2251 g Sigma G7400, 1945 IU, available from Sigma Chemical Company) was added to the bottle and rolled overnight at room temperature. The product was stored overnight at 4° C. in a cold room.

The resulting solid product was dissolved in acidified distilled water (0.617 g in 99.4 g water, 0.035 g 10% HCl) using a stainless steel propeller stirring vigorously overnight. An iodometric assay of aldehyde ($I_2$+CHO→COOH+ $2I^-$) using titration of excess $I_2$ with thiosulfate showed that the solution contained 0.67 milliequivalents/g of CHO (theoretical full reaction at $C_6$ is 2.06 meq/g).

EXAMPLE 2

This example shows the treatment of cationic guar powder and the resulting lap shear bond strength performance compared to that of the unoxidized product. A 2 ounce wide-mouth jar was charged with 2.18 g of Galactosol SP813D cationic guar powder (available from Hercules Incorporated, 91.9% solids), 0.276 g of Sigma C10 catalase (available from Sigma Chemical Company, 3977 IU/IU of galactose oxidase), and 0.225 g of galactose oxidase (SIGMA 7400, 1945 IU, 972 IU/g guar). The mixture was rolled for approximately 48 hours. The final dry powder had the appearance of cinnamon sugar after storage 72 hours at room temperature a solution was prepared at 0.2% guar solids in acidified water as described in Example 1.

The lap shear test specimen (0.01% solution) made with the oxidized guar above broke outside the overlap area, indicating a bond strength of at least 300 psi. The test of unoxidized SP813D guar at the same concentration gave a bond strength of 197 psi.

EXAMPLE 3

This example demonstrates the use of grinding the unmodified (neutral) shredded guar with catalase and galactose oxidase enzymes producing the solid oxidized guar product of this invention. The enzymatic oxidation proceeds as the ground guar is stored at room temperature.

Unmodified shredded guar was ground in a mortar and pestle to produce crude ground starting guar solids (41% water content). Catalase (Sigma C40, 0.601 g) was further ground with 8.94 g of the guar solids to give fine particles, and 0.563 g of Sigma G7400 galactose oxidase was added with grinding. The resulting particles were mixed on a vortex mixer for 45 minutes and then tumbled at 8 rpm at room temperature in a wide mouth bottle for 24 hours to give a solid oxidized guar product. After 48 hours of storage at room temperature, 0.191 g of the product was dissolved in 4.819 g of 0.1N NaOH solution to make a solution wherein the galactose oxidase was completely inactivated. An iodometric assay of the solution showed the guar contained 0.79 meq/g of aldehyde ($I_2$ reaction equivalents). The lap shear test at 0.001% showed 157 psi bond strength for the oxidized guar vs. 125 psi for the base-only-treated (unoxidized) neutral guar.

EXAMPLE 4

This example illustrates the enzyme treatment of shredded guar and the resulting improvement in paper strength for oxidized guar compared to unoxidized guar.

Shredded neutral guar was ground with a mortar and pestle to give a powdered guar designated (55.9% solids). To 8.94 g of this powder was added 0.600 g catalase (Sigma C40, 9×10$^6$ IU) and 0.563 g of SigmaG7400 galactose oxidase (4860 IU) with grinding after each addition. The mixture was tumbled at room temperature for 72 hours.

The solid mixture prepared above (9.015 g, 4.7 g solids) was added to 2340 g of pure water and stirred vigorously to produce a 0.2% solution of the product for paper testing. Paper handsheets (80 lb/3000 ft$^2$ basis weight, bleached kraft pulp, 1% additive based on pulp weight) were prepared according to the general procedure described above. Paper with no additive had normalized dry tensile strength of 41.5 lb/in. Unoxidized neutral guar gave 41.8 lb/in, while the oxidized guar product had normalized dry tensile strength of 50.6 lb/in.

EXAMPLE 5

Air Blending Dry Guar With Dry Catalase and Galactose Oxidase 0.50 g of catalase (SigmaC40) was added to 10.85 g of Galactosol SP813D (91.9% solids) cationic guar at a low setting in an Oster blender. After 15 seconds at the low setting, 0.241 g of galactose oxidase (Worthington Cat. No. 4523 available from Worthington Biochemical Co.) was added and blending was continued for 15 seconds to give an even colored, well mixed blend. After a one day storage at room temperature, a 0.2% aqueous solution of the blend was titrated iodometrically indicating 64% oxidation of the galactose in the guar to aldehyde. The lap shear test showed a bond strength of 246 psi for this sample.

EXAMPLE 6

Oxidation of Aqueous Slurry of Guar 11.14 g of Supercol U guar (9.9 g solids), available from Hercules Incorporated) was dispersed in 88.7 g of water to give a continuous gel filling a wide mouth jar. The jar was tumbled for six days giving a slurry of gel particles which could be stirred easily.

5.5 g of 0.05M K$_2$HPO$_4$ buffer solution and 0.1791 g catalase (SigmaC40) was added to 10 g of the guar slurry. 0.1127 g galactose oxidase (SigmaG7400) was added as a solution in 5.5 ml. of water, the pH being adjusted to 7 with K$_2$HPO$_4$ buffer. The resulting 4.7% solids slurry was stirred gently for 17 hrs to give 48% oxidation of galactose in the guar and a lap shear of 154 psi vs 125 psi for unoxidized guar.

EXAMPLE 7

Oxidation of Guar in Aqueous Slurry In the Presence of Nonsolvent For the Guar 1.4875 g of t-butylalcohol and 0.02 g of 1,2-benzisothiazolin-3-one was dissolved in 3.4707 g of water. To the resulting solution was added 0.1125 g of galactose oxidase (SigmaG7400), 0.1800 g of catalase (SigmaC40) and 1.1142 g of Supercol U guar to give an insoluble hazy guar slurry that was easily stirred. After two days of stirring at room temperature the galactose in the guar was 43% oxidized.

EXAMPLES 8 TO 11

A number of gums, all oxidizable galactose type of alcohol configuration containing polymers were dry mixed with galactose oxidase, catalase and Proxel to give aldehyde by oxidation. The following table shows the amounts of gum, galactose oxidase, catalase and Proxel (1,2-benzisothiazolin-3-one) that were dry mixed. The aldehyde produced is assayed in a solution of the product. The assay is performed by the aldehyde by dinitrosalicylic acid which is determined colorimetrically by the procedure described by Ghose in *Pure & Application Chemistry,* 59, pg 257 (1987).

| GUM g | GALACTOSE OXIDASE 540 IU/g of gum mg | CATALASE 1000 IU/IU of galactose oxidase | PROXEL mg | MICRO-MOLES CHO/mg |
|---|---|---|---|---|
| Larch[1] 0.1675 | 4.4 | 8.5 | 1.6 | 0.486 |
| Tara[2] 0.1678 | 4.4 | 7.7 | 1.9 | 0.678 |
| Locust Bean[3] 0.1734 | 4.4 | 8.1 | 1.5 | 0.715 |
| Tragacanth[4] 0.1715 | 4.4 | 8.1 | 1.5 | 0.193 |

[1]Larch (Sigma Lot# 31H7751)
[2]Tara Polygum 43/1 available from AEP Colloids Company
[3]Locust Bean (Sigma G0753)
[4]Tragacanth (Sigma G1128)

What is claimed is:

1. A composition comprising (a) a polymer which is in solid state and contains groups having oxidizable galactose type of alcohol configuration and (b) galactose oxidase, wherein the groups having oxidizable galactose type of alcohol configuration are described by the following chemical structures

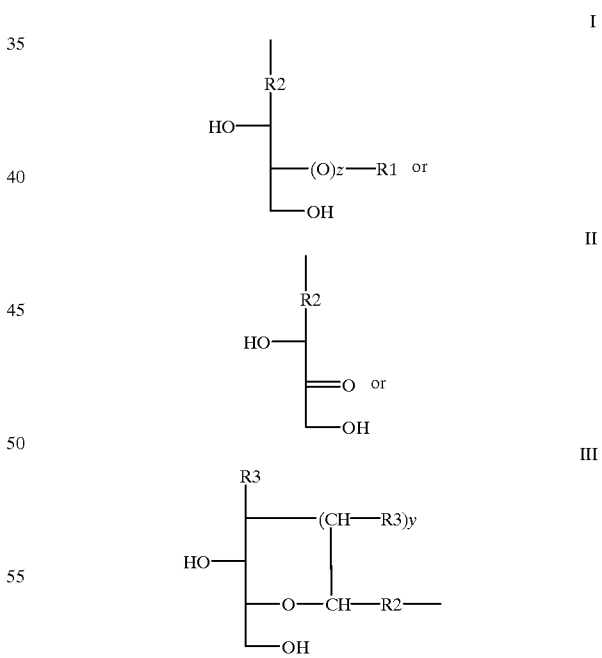

where R1 is an alkyl group of the formula C(n)H(2n+1) where n is 0 to 20: z is 0 or 1; where R2 is a linking group composed of an alkylene or an aromatic alkylene or an alkylene ether, or an alkylene ester, or an alkylene amide, or an alkylene urethane diradical where said linking group has a total number of carbons from 2 to 20; where R3 is —H, —OH, —OCH$_3$, —OC$_2$H$_5$, —OC$_3$H$_7$, —OC$_4$H$_9$, —OOCR5, (where R5 is alkyl radical of 1 to 5 carbons), —NH$_2$, —NH—CO—R5; and y is 0 or 1; and wherein the oxidizable galactose type of alcohol group containing polymer is selected from the group consisting of galactomannan gums or their ether derivatives, arabinogalactan gums their ether derivatives, carubin, lichenan, tamarind and potato galactan galactoglucomannan hemicelluloses or their ether derivatives and synthetically or enzymatically modified polymers selected from the group consisting of polysaccharides, polyacrylamides, polyacrylates, polyamides polyvinyl alcohol, and polyvinyl acetate, and wherein the lower limit of oxidizable galactose type of alcohol group containing polymer is about 50% based upon the weight of the composition.

2. The composition of claim 1 wherein the lower limit of oxidizable galactose type of alcohol group containing polymer is about 50% based upon the weight of the composition, and the lower limit of galactose oxidase is about 10 units/g of oxidizable galactose type of alcohol configuration containing polymer.

3. The composition of claim 1 wherein the lower limit of oxidizable galactose type of alcohol group containing polymer is about 50% based upon the weight of the composition, and the upper limit of galactose oxidase is about 3,000 units/g of oxidizable galactose type of alcohol group containing polymer.

4. The composition of claim 1 wherein the upper limit of oxidizable galactose type of alcohol configuration containing polymer is about 100% based upon the weight of the composition, and the upper limit of galactose oxidase is about 3,000 units/g of oxidizable galactose type of alcohol group containing polymer.

5. The composition of claim 1 wherein the amount of oxidizable galactose type of alcohol configuration containing polymer is from about 50 to about 100% based upon the weight of the composition, and the amount of galactose oxidase is from about 10 to about 3,000 units/g of oxidizable galactose type of alcohol configuration containing polymer.

6. The composition of claim 5 wherein the oxidizable galactose type of alcohol configuration containing polymer is selected from the group consisting of polysaccharides containing at least 20 mole % of galactose.

7. The composition of claim 5 wherein the lower limit of oxidizable galactose type of alcohol configuration containing polymer is about 70% based upon the weight of the composition, and the lower limit of galactose oxidase is about 25 units/g of oxidizable galactose type of alcohol configuration containing polymer.

8. The composition of claim 5 wherein the upper limit of oxidizable galactose type of alcohol group containing polymer is about 98% based upon the weight of the composition, and the upper limit of galactose oxidase is about 2,000 units/g of oxidizable galactose type of alcohol group containing polymer.

9. The composition of claim 5 wherein the galactomannan gum is selected from the group consisting of guar, locust bean, tara and fenugreek gum or their ether derivatives; the arabinogalactan gum is selected from the group consisting of arabic, larch and tragacanth gum or their ether derivatives, and the synthetically or enzymatically modified polymer is selected from the group consisting of polyacrylamides, polyacrylates, polyamides, polyvinyl alcohol, and polyvinyl acetate, and polysaccharides containing less than 20% galactose type groups based on the weight of the modified polymer.

10. The composition of claim 6 wherein the amount of oxidizable galactose type of alcohol group containing polymer is from about 50% to about 98% based upon the weight of the composition, and the amount of galactose oxidase is from about 25 to about 2,000 units/g of oxidizable galactose type of alcohol group containing polymer.

11. The composition of claim 9 wherein the amount of oxidizable galactose type of alcohol group containing polymer is from about 50% to about 98% based upon the weight of the composition, and the amount of galactose oxidase is from about 25 to about 2,000 units/g of oxidizable galactose type of alcohol group containing polymer.

12. The composition of claim 11 wherein the oxidizable galactose type of alcohol group containing polymer is selected from the group consisting of cationic guar, anionic guar, amphoteric guar, hydroxypropyl guar, dihydroxypropyl guar and hydroxyethyl guar.

13. The composition of claim 11 wherein the lower limit of oxidizable galactose type of alcohol group containing polymer is about 85% based upon the weight of the composition.

14. The composition of claim 11 wherein the upper limit of oxidizable galactose type of alcohol group containing polymer is about 95% based upon the weight of the composition.

15. A process for the oxidation of a polymer containing groups having an oxidizable galactose type of alcohol configuration comprising: providing the oxidizable galactose type of alcohol configuration containing polymer which is in solid state and galactose oxidase, and contacting them wherein the groups having the oxidizable galactose type of alcohol configuration are described by the following chemical structures

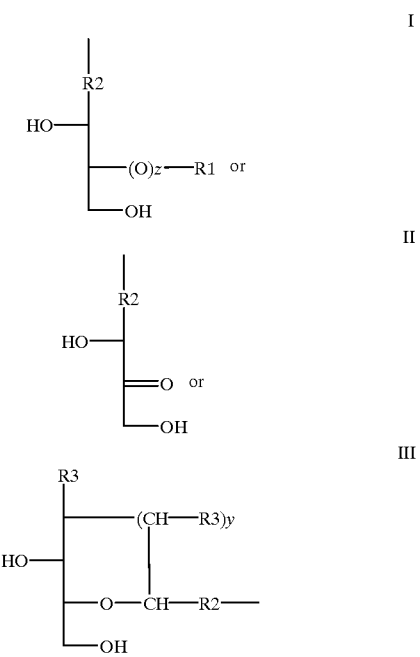

where R1 is an alkyl group of the formula C(n)H(2n+1) where n is 0 to 20: z is 0 or 1, where R2 is a linking group composed of an alkylene or an aromatic alkylene or an alkylene ether, or an alkylene ester, or an alkylene amide, or an alkylene urethane diradical where said linking groups has a total number of carbon from 2 to 20; where R3 is —H, —OH, —OCH$_3$, —OC$_2$H$_5$, —OC$_3$H$_7$, —OC$_4$H$_9$, —OOCR5, (where RS is alkyl radical of 1 to 5 carbons), —NH$_2$, —NH—CO—R5, and y is 0 or 1; and wherein the oxidizable galactose type of alcohol group containing polymer is selected from the group consisting of galactomannan gums or their ether derivatives, arabinogalactan gums or their ether derivatives, galactoglucomannan hemicelluloses or their ether derivatives and synthetically or enzymatically modified polymers selected from the group consisting of polysaccharides, polyacrylamides, polyacrylates polyamides, polyvinyl alcohol, and polyvinyl acetate, and wherein the lower limit of oxidizable galactose type of alcohol configuration containing polymer is about 50% based upon the weight of the composition.

16. The process of claim 15 wherein the galactose oxidase is in solid state, the lower limit of oxidizable galactose type of alcohol group containing polymer is about 50% by weight, and the lower limit of galactose oxidase is about 10 units/g of oxidizable galactose type of alcohol configuration containing polymer.

17. The process of claim 15 wherein the galactose oxidase is in solid state, the upper limit of oxidizable galactose type of alcohol group containing polymer is about 100% by weight, and the upper limit of galactose oxidase is about 3,000 units/g of oxidizable galactose type of alcohol configuration containing polymer.

18. The process of claim 15 wherein the oxidizable galactose type of alcohol configuration containing polymer which is in solid state is contacted with the galactose oxidase in aqueous medium such that less than about 0.1% by weight of oxidizable galactose type of alcohol configuration containing polymer, based upon the weight of the aqueous medium, is dissolved in the aqueous medium, the lower limit of oxidizable galactose type of alcohol configuration containing polymer is about 50% by weight of oxidizable galactose type of alcohol configuration containing polymer, the aqueous medium, and the galactose oxidase and the upper limit of galactose oxidase is about 3,000 units/g of oxidizable galactose type of alcohol configuration containing polymer.

19. The process of claim 15 wherein the oxidizable galactose type of alcohol group containing polymer is selected from the group consisting of cationic guar, anionic guar, amphoteric guar, hydroxypropyl guar, dihydroxypropyl guar and hydroxyethyl guar.

20. The process of claim 19 wherein the galactose oxidase is in solid state, the lower limit of oxidizable galactose type of alcohol group containing polymer is about 70% by weight, and the lower limit of galactose oxidase is about 25 units/g of oxidizable galactose type of alcohol configuration containing polymer.

21. The process of claim 19 wherein the galactose oxidase in solid state, the upper limit of oxidizable galactose type of alcohol group containing polymer is about 98% by weight, and the upper limit of galactose oxidase is about 2,000 units/g of oxidizable galactose type of alcohol configuration containing polymer.

22. The process of claim 15 wherein the oxidizable galactose type of alcohol group containing polymer which is in solid state is contacted with the galactose oxidase in aqueous medium such that less than about 0.1% by weight of the oxidizable galactose type of alcohol group containing polymer, based upon the weight of the aqueous medium, is dissolved in the aqueous medium and the lower limit of oxidizable galactose type of alcohol group containing polymer is about 6% by weight.

23. The process of claim 15 comprising dry mixing the ingredients.

24. The process of claim 15 comprising dry mixing the ingredients.

25. The composition of claim 1 wherein the synthetically or enzymatically modified polymer is selected from the group consisting of polyacrylates, polyacrylamides, polyamides, polyvinyl alcohol, polyvinyl acetate, and polysaccharides containing less than 20% galactose type groups based on the weight of the modified polymer.

26. The process of claim 15 wherein the synthetically or enzymatically modified polymer is selected from the group consisting of polyacrylates, polyacrylamides, polyamides, polyvinyl alcohol, polyvinyl acetate, and polysaccharides containing less than 20% galactose type groups based on the weight of the modified polymer.

27. The composition of claim 25 where the synthetically or enzymatically modified polymer is selected from the group consisting of starch and polyacrylates.

28. The process of claim 26 where the synthetically or enzymatically modified polymer is selected from the group consisting of starch and polyacrylates.

* * * * *